United States Patent
Kuan et al.

(10) Patent No.: US 10,106,832 B2
(45) Date of Patent: Oct. 23, 2018

(54) METHOD FOR MANUFACTURING A MICROBIAL DETECTION DEVICE, MICROBIAL DETECTION METHOD, MICROBIAL DETECTION KIT, AND MICROBIAL DETECTION DEVICE

(71) Applicant: NATIONAL TSING HUA UNIVERSITY, Hsinchu (TW)

(72) Inventors: Chen-Meng Kuan, Hsinchu (TW); Robert S. Langer, Newton, MA (US); Chao-Min Cheng, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 0 days.

(21) Appl. No.: 15/235,791

(22) Filed: Aug. 12, 2016

(65) Prior Publication Data

US 2017/0058311 A1    Mar. 2, 2017

(30) Foreign Application Priority Data

Sep. 1, 2015 (TW) .............................. 104128870 A

(51) Int. Cl.
| | |
|---|---|
| C12Q 1/04 | (2006.01) |
| C12Q 1/06 | (2006.01) |
| C12Q 1/32 | (2006.01) |
| C12Q 1/10 | (2006.01) |
| G01N 21/75 | (2006.01) |
| C12Q 1/14 | (2006.01) |

(52) U.S. Cl.
CPC ............... *C12Q 1/10* (2013.01); *C12Q 1/04* (2013.01); *C12Q 1/06* (2013.01); *C12Q 1/14* (2013.01); *C12Q 1/32* (2013.01); *C12Q 2304/24* (2013.01); *G01N 2021/752* (2013.01); *G01N 2333/245* (2013.01); *G01N 2333/31* (2013.01); *G01N 2333/90209* (2013.01)

(58) Field of Classification Search
None
See application file for complete search history.

(56) References Cited

U.S. PATENT DOCUMENTS

| | | |
|---|---|---|
| 4,061,468 A | 12/1977 | Lange et al. |
| 5,063,153 A * | 11/1991 | Arai ................... C12Q 1/32 422/423 |
| 6,149,952 A | 11/2000 | Horan |
| 2007/0048182 A1 | 3/2007 | Song et al. |
| 2013/0089858 A1 | 4/2013 | Wong, Jr. et al. |
| 2015/0010904 A1 | 1/2015 | Wong, Jr. et al. |
| 2015/0017639 A1 | 1/2015 | Wong, Jr. et al. |
| 2015/0018247 A1 | 1/2015 | Tseng et al. |
| 2015/0132742 A1 | 5/2015 | Thuo et al. |
| 2015/0168394 A1 | 6/2015 | Wong, Jr. et al. |

FOREIGN PATENT DOCUMENTS

| | | |
|---|---|---|
| CN | 103389303 A | 11/2013 |
| EP | 1 920 251 B1 | 12/2010 |
| TW | 201317361 A | 5/2013 |
| TW | 201502514 A | 1/2015 |
| WO | WO 2013/181656 A1 | 12/2013 |

OTHER PUBLICATIONS

ExPASy. Diaphorase. Datasheet [online]. SIB.Swiss Institute of Bioinformatics [retrieved on Jan. 7, 2018]. Artimo, P. et al. 2012. ExPASy: SIB bioinformatics resource portal. Nuc. Acids Res. 40(W1): W597-W603.Internet: <URL: http://enzyme.expasy.org/cgi-bin/enzyme/enzyme-search-ful?keywords=diaphorase, pp. 1-3.*

* cited by examiner

*Primary Examiner* — Renee Claytor
*Assistant Examiner* — Sharon M. Papciak
(74) *Attorney, Agent, or Firm* — Muncy, Geissler, Olds & Lowe, P.C.

(57) ABSTRACT

The present invention provides a method for manufacturing a microbial detection device, microbial detection method, microbial detection kit and microbial detection device. The manufacturing method includes the following steps: defining a sampling portion and a reaction portion on a substrate. Fiber materials are disposed in the reaction portion and a surface of the reaction portion which contacts with the fiber materials comprises abundant hydroxyl groups. Reaction reagents are then added into the fiber materials. An acidic solution is applied to treat the fiber materials and the hydroxyl groups in the reaction portion.

6 Claims, 10 Drawing Sheets

METHOD FOR MANUFACTURING A MICROBIAL DETECTION DEVICE, MICROBIAL DETECTION METHOD, MICROBIAL DETECTION KIT, AND MICROBIAL DETECTION DEVICE

CROSS REFERENCE TO RELATED APPLICATION

This application claims the benefits of the Taiwan Patent Application Serial Number 104128870, filed on Sep. 1, 2015, the subject matter of which is incorporated herein by reference.

BACKGROUND OF THE INVENTION

1. Field of the Invention

The present invention relates to a manufacturing method, a detection method, a device, and a kit. More specifically, the present invention relates to a manufacturing method of a microbial detection device, a detection method, a device, and a kit for microbial detection.

2. Description of Related Art

The microbial detection becomes more important in food safety detections and infection control in medical premises. Microbial contamination may occur due to improper food processing or if the medical worker or surgical instruments fail to fully sterilize before surgery. The common microbial contamination caused by food processing is *E. coli* O157:H7 in drinking water; and the common microbial contamination occurs in medical premises is Methicillin-resistant *Staphylococcus aureus* (MRSA). The former contamination may cause bloody diarrhea to those infected, and the latter may prolonged hospitalization of the patients or even cause death.

The detections of numbers and activity of pathogenic microorganism are rather important when studying the contamination of food, water, or medical premises. The common microbial counting methods are turbidimetry, erythrocytomertry, and colony counting method.

However, each aforementioned counting method has its disadvantages. For example, the number of microorganisms may be rapidly obtained by turbidimetry and erythrocytomertry, but the activity of the microorganism cannot be determined, or the components of the test solution and the metabolites of the microorganism may easily affect the detection and cause false positive results. The colony counting method includes the steps of sequentially diluting the test sample and coating the diluted test sample on the culture medium. The number of the living microorganism may then be determined, but the colony counting method is inapplicable for large quantities of test samples due to its complex operation process, poor reproducibility, and time-consuming. Furthermore, the aforementioned methods rely on high-level detection equipment; therefore, the detection should be conducted in a laboratory which is time-consuming and labor-intensive.

With the awareness of health and food safety, the concept of household self-detection is growing. Household self-detection refers to conducting the detection by people at their home. Usually, the detection of contamination or sign of infection may be determined immediately by observing the color change of the test strip with bare eyes without using equipment or with simple equipment. Moreover, if the color change of the test strip is too significant, further detail detections may be conducted at professional premises. Accordingly, household self-detection has advantages of convenience and money saving. Recently, the household detection for water or food safety is based on the principle of colorimetry or polarimetry, and test strips added with detection reagent are used for the detection. The users may compare the color of the test strip with the standard color table to determine the number of microorganism in the test sample. This simple detection method is convenience and safe for the public, however, the conventional test strips usually are processed by numerous processing steps, the substances added during those processing steps (such as bleach comprising chlorine or other toxic chemical substances) may cause the safety issues to the test strips.

Accordingly, it is desirable to provide a method for manufacturing a microbial detection device, microbial detection method, microbial detection kit, and microbial detection device, which can be easily operated as the test strips but is safe for practical usage, and the detection speed thereof is controllable.

SUMMARY OF THE INVENTION

According to the aforementioned problems, the object of the present invention is to provide a manufacturing method of a microbial detection device, a microbial detection method, a kit and a device for microbial detection. Those provided by the present invention are advantageous for easy operation, analysis speed controllability, and practical application safety.

To achieve the object, the manufacturing method of a microbial detection device of the present invention comprises the following steps: defining a sampling zone and a reacting zone on a substrate; disposing a fiber material in the reacting zone wherein the surface of the reacting zone which contacts with the fiber material comprises abundant hydroxyl groups; adding a reacting reagent onto the fiber material, and applying an acidic solution to treat the fiber material and the hydroxyl group.

In one embodiment of the present invention, the reacting reagent comprises at least one selected from a group consisting of 5-methylphenazinium methosulfate and diaphorase; and at least one selected from a group consisting of 3-(4,5-Dimethylthiazol-2-yl)-2,5-diphenyltetrazolium bromide (MTT), (2-(4-iodophenyl)-3-(4-nitrophenyl)-5-phenyl-2H-tetrazoliumchloride (INT), water-soluble tetrazolium salts (WSTs), and (2,3-bis-(2-methoxy-4-nitro-5-sulfophenyl)-2H-tetrazolium-5-carboxanilide (XTT).

In one embodiment, the fiber material is α-cellulose particles.

In one embodiment, the acidic solution contacts the surface of the reacting zone to treat those hydroxyl groups after the acidic solution penetrates through the fiber material.

In one embodiment, the substrate is a fibrous substrate.

In one embodiment, the reacting zone has an accommodating space, wherein the accommodating space is formed on a surface of the substrate and the fiber material is disposed in the accommodating space.

To achieve the object, the present invention provides a microbial detection method, which comprises the following steps: providing a detection device, wherein the detection device comprises a first substrate, the first substrate comprises a sampling zone and a reacting zone, the reacting zone includes the fiber material and a reacting reagent, the fiber material and hydroxyl groups on a surface of the reacting zone which contact with the fiber material are treated with an acidic solution; and providing a test sample to contact with the reacting zone and reacting with the reacting reagent.

In one embodiment, the fiber material is α-cellulose particles.

In one embodiment, the steps of providing the test sample to contact with the reacting zone and reacting with the reacting reagent comprise: providing the test sample to contact with the sampling zone, and the test sample being moved from the sampling zone toward the reacting zone to react with the reacting reagent.

In one embodiment, the microbial detection method further comprises the steps of removing the fiber material; and adding an alkaline solution to the reacting zone after the steps of providing the test sample to contact with the reacting zone and reacting with the reacting reagent.

In one embodiment, the alkaline solution is transported to the reacting zone in a transporting direction by a second substrate, and the transporting direction is essentially perpendicular to a moving direction of which the test sample moves from the sampling zone to the reacting zone.

In one embodiment, the hydrophilicity of the first substrate is higher than that of the second substrate.

In one embodiment, the first substrate further includes a transporting zone, wherein the transporting zone connects with the sampling zone and the reacting zone, and the reacting zone is disposed on a section of the transporting zone.

In one embodiment, the reacting zone further comprises a first reacting zone and a second reacting zone, which are disposed on different sections of the transporting zone.

In one embodiment, the reacting reagent comprises at least one selected from a group consisting of methylphenazinium methosulfate and diaphorase; and at least one selected from a group consisting of 3-(4,5-Dimethylthiazol-2-yl)-2,5-diphenyltetrazolium bromide (MTT), (2-(4-iodophenyl)-3-(4-nitrophenyl)-5-phenyl-2H-tetrazoliumchloride (INT), water-soluble tetrazolium salts (WSTs), and (2,3-bis-(2-methoxy-4-nitro-5-sulfophenyl)-2H-tetrazolium-5-carboxanilide (XTT).

To achieve the aforementioned subject, the present invention provides a microbial detection kit, which comprises: a detection device and an acidic solution. The detection device includes a substrate having a sampling zone and a reacting zone, wherein the reacting zone includes a fiber material and a reacting reagent. The reacting reagent comprises at least one selected from a group consisting of 5-methylphenazinium methosulfate and diaphorase; and at least one selected from a group consisting of 3-(4,5-Dimethylthiazol-2-yl)-2,5-diphenyltetrazolium bromide (MTT), 2-(4-iodophenyl)-3-(4-nitrophenyl)-5-phenyl-2H-tetrazoliumchloride (INT), water-soluble tetrazolium salts (WSTs), and (2,3-bis-(2-methoxy-4-nitro-5-sulfophenyl)-2H-tetrazolium-5-carboxanilide (XTT). The acidic solution is utilized for treating the fiber material and the hydroxyl groups on a surface of the reacting zone which contact with the fiber material.

In one embodiment of the present invention, the fiber material is α-cellulose particles.

In one embodiment of the present invention, the fiber material is disposed on the reacting zone after treated by the acidic solution.

To achieve the aforementioned subject, the present invention provides a detection device, which comprises a substrate having a sampling zone and a reacting zone. The reacting zone includes a fiber material; and a reacting reagent, wherein the reacting reagent comprises at least one selected from a group consisting of methylphenazinium methosulfate and diaphorase; and at least one selected from a group consisting of 3-(4,5-Dimethylthiazol-2-yl)-2,5-diphenyltetrazolium bromide (MTT), (2-(4-iodophenyl)-3-(4-nitrophenyl)-5-phenyl-2H-tetrazoliumchloride (INT), water-soluble tetrazolium salts (WSTs), and (2,3-bis-(2-methoxy-4-nitro-5-sulfophenyl)-2H-tetrazolium-5-carboxanilide (XTT); wherein the fiber material and hydroxyl groups of a surface of the reacting zone which contact with the fiber material are treated with an acidic solution.

In summary, the reacting zone disposed with fiber material and reacting reagent is applied to the manufacturing method of the microbial detection device, the microbial detection method, the microbial detection kit, and device to detect the microbial in vivo. For example, the numbers of *Escherichia coli* or *staphylococcus* in drinks or foods, or the detection or screening of bacteria or infectious at medical places or pre-surgery infection control. Also, the microbial detection device is advantageous of lower cost and easy processing. The reacting zone disposed with fiber material may reduce the transfer rate of the test sample and increase the reacting area so that the reaction rate and the reacting time may be increased for enhancing the reaction signal. The addition of the acidic solution may gelatinize the fiber material and moisturize the fiber material, therefore, the test sample may easily react at the reacting zone and result in an obvious reaction signal. In comparison, the test sample needs not to be incubated before detection, and whether a test sample contains a certain amount of the microbial may be detected rapidly with the advantageous of easy operation according to the manufacturing method of the microbial detection device, the microbial detection method, the microbial detection kit and device of the present invention. In addition, the manufacturing method of the microbial detection device, the microbial detection method, the microbial detection kit and device utilize the acidic solution to pretreat the fiber material before the detection reaction, accordingly, the hydroxyl groups, which may interrupt the detection reaction of MTT, in the substrate may be neutralized to reduce the false negatives detection and increase the sensibility of detection.

DETAILED DESCRIPTION OF THE PREFERRED EMBODIMENT

A detection device of a preferred embodiment of the present invention will be described from the following description with the accompanying drawings, wherein the same elements will be labeled with same reference symbols.

Figure 1A:
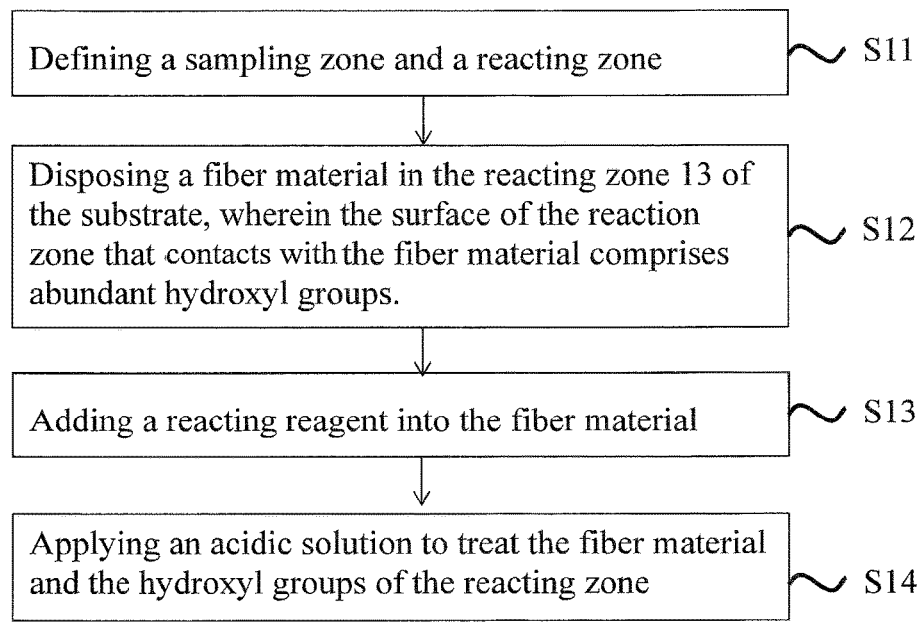
FIG. 1A is a flow chart of the method of manufacturing the microbial detection device of a preferred embodiment of the present invention.
Figure 1B:
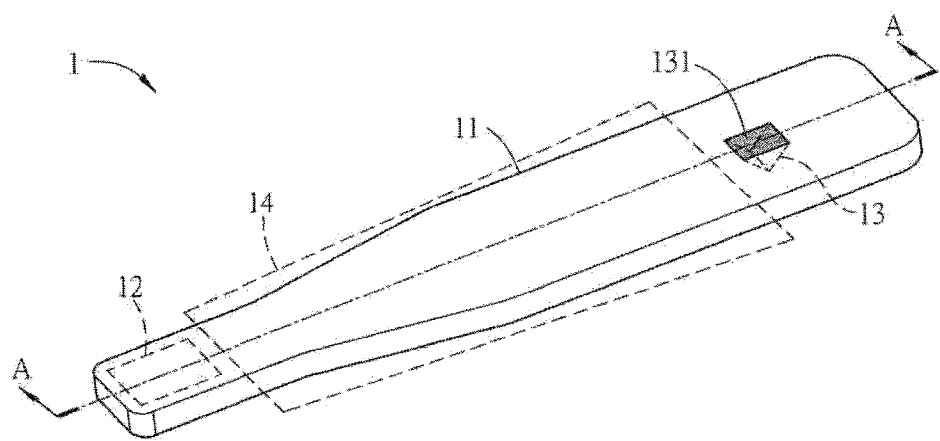
FIG. 1B is the schematic diagram of the microbial detection device manufactured by the method shown in FIG. 1A.
Figure 3:
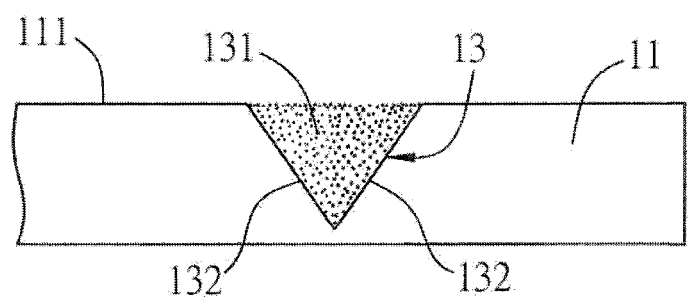
FIG. 3 is the cross-section view along line A-A of the microbial detection device shown in FIG. 1B.

First, please refer to FIG. 1A, FIG. 1B, FIG. 3 at the same time, wherein FIG. 1A illustrates a flowchart of the manufacturing method of the microbial detection device; FIG. 1B illustrates the microbial detection device manufactured by the manufacturing method illustrated in FIG. 1A; and FIG. 3 illustrates the cross-section view along line A-A in FIG. 1B.

The application of the microbial detection device 1 manufactured by the manufacturing method of the microbial detection device of the present preferred embodiment is not particularly limited to certain types of test samples and is applicable of food safety detections and biomedical detections. In terms of food safety detections, the microbial detection device of the preferred embodiment may be applied for detecting the numbers of *Escherichia coli* or *staphylococcus* to prevent food poisoning. In terms of biomedical detections, the microbial detection device of the preferred embodiment may be applied for determining if an inflammatory reaction of a patient is caused by bacterial infection (such as urethral infections, corneal infections, or vaginal infections); pre-surgery bacterial detections (such as wound healing of open fractures or arthroscopy surgery); or screening infectious diseases (such as tuberculosis). In the preferred embodiment, the term "microbial" refers to eukaryotic cells, bacteria, fungi and the like.

The manufacturing method of the microbial detection device of the preferred embodiment comprises the following steps: step S11: defining a sampling zone 12 and a reacting zone 13 on a substrate 11. The substrate 11 of the present embodiment may be a fibrous substrate, glass, or polydimethylsiloxane (PDMS). The fibrous substrate may be a lignocellulosic substrate, cotton, or paper, wherein "lignocellulosic substrate" refers to lignified fibrous tissues of plants, and the lignified fibrous tissues refer to the plant tissue developing internally from the cambium. Preferably, the lignified fibrous tissues comprise the cellulose, hemicellulose, pectin, and/or lignin, which have better attraction force to water molecule. Therefore, the test sample from the sampling zone 12 may be transported to the transporting zone 14 and the reacting zone 13 sequentially through the inner tunnels of the lignocellulosic substrate by capillarity force. The method of inputting the test sample to the microbial detection device 1 is not limited, for example, the test sample may contact to the reacting zone 13 directly and react with the reacting reagent to reduce the time needed for the detection process, and to reduce the consumption amount during the transporting process.

If the substrate 11 of the microbial detection device 1 of the preferred embodiment is a lignocellulosic substrate, the source thereof may be wood or bamboo, and is preferably selected from xylophytas with more developed lignified fibrous tissues, such as shrubs or arbor. In practice, the substrate may be a stir bar, wooden chopsticks, or toothpicks made from lignified fibrous tissues. In addition, when the substrate 11 is made of glass or PDMS, channels of microfluidic channels may be formed simultaneously in the present step for transmitting the test samples via capillarity action during the follow-up detection.

Also, in the present embodiment, the substrate 11 made of lignified fibrous tissues of the microbial detection device 1 refers to at least a portion of the substrate 11 which is made of lignified fibrous tissues. In the actual manufacturing process, the whole substrate is preferably made of lignified fibrous tissues. Apparently, the scope of the present invention includes the case that portion of the substrate 11 where the test samples flow through is made of lignified fibrous tissue wherein the lignified fibrous tissue is served as a "flow channel".

In some embodiments, a transporting zone 14 is further disposed on the substrate 11, and the transporting zone 14 connects with the sampling zone 12 and the reacting zone 13. Practically, the shape or size of each zone are not particularly limited and therefore may be designed according to the test sample and the detection target. In practice, the shape of each zone may comprise cylindrical, rectangular, plate, or the like, but the present invention is not limited thereto.

Next, step S12: disposing a fiber material in the reacting zone 13 of the substrate 11. The "fiber material" refers to a natural fiber or artificial fiber, and preferably a hydrophilic fiber material comprising cellulose. The exemplified fiber material of the present embodiment is α-cellulose particles 131 wherein the particle size thereof is not limited, which may be particles with larger particle size to powders with micro-scale particle size). The surface 132 of the reaction zone 13 that contacts with the α-cellulose particles 131 comprises abundant hydroxyl groups, which may interfere the reaction between the test sample and the reaction reagent. Accordingly, the following treating processes are necessary for reducing the instability of the test result given by the microbial detection device 1.

Please refer to FIG. 3, in this preferred embodiment, the reacting zone 13 may comprise an accommodating space wherein the surface 111 of the substrate 11 is formed therein and the α-cellulose particles 131 are also disposed therein. In addition, in the present embodiment, the accommodating space is illustrated as a V-shaped notch in FIG. 3; however, the shape or size of the notch is not particularly limited and may be formulated as needed. The notch illustrated in FIG. 1B and FIG. 3 is only exemplary and the present invention is not limited thereto. In practical usage, the shape of the accommodating space is not limited to cuboid, cube, cylinder, hemisphere, V-shaped, shapes other than the aforementioned shapes, or combination thereof. In the present invention, the position of the reacting zone 13 is not limited and may be formulated based on different detection needs.

Next, step S13: adding a reacting reagent into the fiber material (α-cellulose particles 131). The reacting reagent comprises at least two reagents, wherein the first reagent is selected from 5-methylphenazinium methosulfate or diaphorase, and the second reagent is selected from 3-(4,5-Dimethylthiazol-2-yl)-2,5-diphenyltetrazolium bromide (MTT), 2-(4-iodophenyl)-3-(4-nitrophenyl)-5-phenyl-2H-tetrazolium chloride (INT), water-soluble tetrazolium salts (WSTs), or 2,3-bis-(2-methoxy-4-nitro-5-sulfophenyl)-2H-tetrazolium-5-carboxanilide (XTT). The water-soluble tetrazolium salts (WSTs) comprises but not limited to: WST-1 (2-(4-Iodophenyl)-3-(4-nitrophenyl)-5-(2,4-disulfophenyl)-2H-tetrazolium), WST-3 (2-(4-Iodophenyl)-3-(2,4-dinitrophenyl)-5-(2,4-disulfophenyl)-2H-tetrazolium), WST-4 (2-Benzothiazolyl-3-(4-carboxy-2-methoxyphenyl)-5-[4-(2-sulfoethylcarbamoyl)phenyl]-2H-tetrazolium), WST-5 (2,2'-Dibenzothiazolyl-5,5'-bis [4-di(2-sulfoethyl)carbamoylphenyl]-3,3'-(3,3'-dimethoxy 4,4'-biphenylene)ditetrazolium), WST-8 (2-(2-methoxy-4-nitrophenyl)-3-(4-nitrophenyl)-5-(2,4-disulfophenyl)-2H-tetrazolium), WST-9 (2-(4-Nitrophenyl)-5-phenyl-3-[4-(4-sulfophenylazo)-2-sulfophenyl]-2H-tetrazolium, monosodium salt), WST-10 (2,5-Di-(4-nitrophenyl)-3-[4-(4-sulfophenylazo)-2-sulfophenyl]-2H-tetr azolium, monosodium salt), and WST-11 (2-(4-Nitrophenyl)-5-(2-sulfophenyl)-3-[4-(4-sulfophenylazo)-2-sulfophenyl]-2H-tetrazolium); and in the present embodiment, WST is preferably WST-1 or WST-8.

Figure 4:
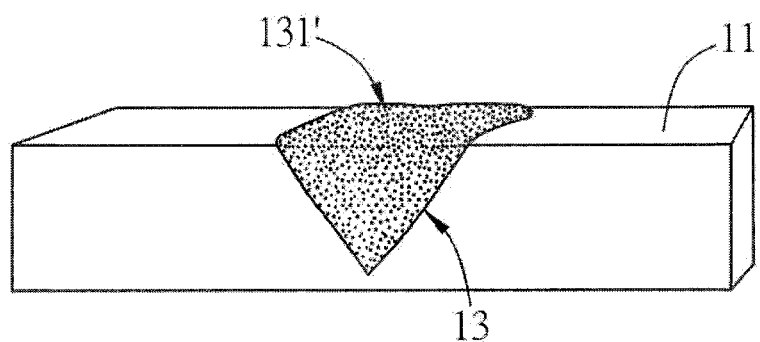
FIG. 4 is the schematic view of the reacting zone of the microbial detection device shown in FIG. 1B after adding the acidic solution into the reacting zone.

Finally, S14: applying an acidic solution to treat the fiber material (α-cellulose 131) and the hydroxyl groups of the reacting zone 13. Please refer to FIG. 4, which illustrates the moist and pasty α-cellulose particles 131' after the acidic solution is applied. The acidic solution in S14 is preferably $HCl$, $HNO_3$, HBr, HI, citric acid, acetic acid, or $H_3PO_4$. As mentioned above, the hydroxyl groups of the α-cellulose particle 131 may interfere the reaction of the reacting reagent, for example, the reaction between 5-methyl-phenazinium methosulfate and 3-(4,5-dimethylthiahiazo-2-yl)-2,5-diphenytetrazoliumromide, or the reaction of succinate dehydrogenase of the test cells. Therefore, the purpose of applying the acidic solution in step S14 is to neutralize the hydroxyl groups of the α-cellulose particles with the hydrogen ions ($H^+$) in the acidic solution. Accordingly, the detection sensitivity may be improved by inhibiting the effect when the hydroxyl groups of the cellulose react with the test sample of the reacting reagent, and inhibiting the reactions which are not reacted with the microorganisms. The ultimate goal of applying the acidic solution is to reduce the false negative of the detections and increase the detection sensitivity. Also, the α-cellulose particles 131' in the reacting zone 13 become pasty and remain moist after applying the acidic solution. The moist and pasty α-cellulose particles 131' in reacting zone 13 make the test sample prone to react with the reacting reagent (such as MTT) in the reacting zone 13 so that the reaction signal becomes more apparent comparing to the case that the α-cellulose particles are completely dry.

In addition, the present invention also provides a microbial detection method. Please refer to FIG. 2 which illustrates a flow chart of the microbial detection method of another preferred embodiment. The microbial detection device 1 manufactured by the aforementioned example is applied for the microbial detection method of the present example, wherein the microbial detection method comprises the following steps. First, step S21: preparing a detection device 1, wherein the detection device 1 comprises a substrate 11 having a sampling zone 12 and a reacting zone 13. The reacting zone 13 includes a fiber material and a reacting reagent, wherein a partial surface of the reacting zone 13 that contacts with the fiber material is treated with an acidic solution. The detection device 1 is shown in FIG. 1B which comprises a substrate 11. The substrate 11 comprises hydroxyl groups, that is, hydroxyl groups are contained in the chemical structure of the material forming the substrate 11. A sampling zone 12 and a reacting zone 13 are disposed on the substrate 11, however, in some embodiments, a transporting zone 14 may be further disposed on the substrate 11 and connect with the sampling zone 12 and reacting zone 13. Practically, the shape and size of each zone is not limited and can be designed based on the test sample or the detection target, for example, those shapes may be but not limited to cylindrical, rectangular, or plate.

The reacting zone 13 includes α-cellulose particles 131 and the reacting reagent, wherein a partial surface 132 of the reacting zone 13 that contacts with the α-cellulose particles 131 is treated with an acidic solution. The description of the applicable reacting reagents in the aforementioned example is incorporated herein, and the same description need not be repeated. Further, the methods of immobilizing the reacting reagent on the reacting zone 13 and/or α-cellulose particles 131 include but not limited to forming covalent bonds between specific functional groups of the reacting reagent and the reacting zone 13 and/or α-cellulose particles 131. The examples of non-immobilized methods may be coating or other similar methods (such as adsorption) to dispose the reacting reagent in the reacting zone and/or α-cellulose particles 131. The method for adsorbing the reacting reagent on the reacting zone 13 and/or α-cellulose particles 131 may be conducted by immersing the reacting zone 13 and/or α-cellulose particles 131 in the solution of the reacting reagent.

In addition, the timing for adding the acidic solution to the α-cellulose particles 131 that contained in the reacting zone 13 may be the time just before conducting the microbial detection, so that the α-cellulose particles 131' contained in the reacting zone 13 may remain moist when conducting the microbial detection. Alternatively, the acidic solution may be added to the reacting zone 13 containing the α-cellulose particles 131 during the manufacturing process of the microbial detection device 1, that is, the α-cellulose particles 131 contained in the reacting zone 13 were pre-treated by the acidic solution to neutralize the hydroxyl groups of the α-cellulose particles 131 before leaving the factory. In order to maintain the moisturized α-cellulose particles 131, the microbial detection device 1 may be vacuum-packed for reservation and for sale by the manufacturer after adding the acidic solution to the reacting zone 13. Accordingly, the microbial detection device 1 may be used for detecting microbial directly without adding the acidic solution to the reacting zone 13 before the detection, and the moist α-cellulose particles 131' is beneficial for the detection reaction condition.

Please refer to FIG. 3 simultaneously, similar to the descriptions of the aforementioned example, the hydroxyl groups of the α-cellulose particles 131 may interfere the chemical reactions between the test sample and the reaction reagent, therefore, the acidic solution is added in step S21 for reducing the false negative of the detection results, increasing the detection sensitivity, and making the test samples easier to react with the reacting reagent in the moist reacting zone 13, so that the reaction signal becomes more apparent.

Further, step S22: providing the test sample (not shown in the figure) to contact with the reacting zone 13 and reacts to the reacting reagent. In step S22, the test sample may be moved to the reacting zone 13 to the sampling zone 12, or the test sample may directly contact with the reacting reagent in the reacting zone 13 without being transmitted by the substrate 11. The mechanism and methods thereof are the same as the aforementioned examples, and the same description need not be repeated.

At last, step S23: detecting the reactions in the reacting zone 13. For example, if the reaction reagent includes 5-methylphenazinium methosulfate and 3-(4,5-dimethyl-thiahiazo-2-yl)-2,5-diphenytetrazoliumromide, the succinate dehydrogenase carried by the microorganism will break the tetrazolium ring of the 3-(4,5-Dimethylthiazol-2-yl)-2, 5-diphenyltetrazolium bromide (MTT) so that the MTT will be reduced to the purple or blue formazan crystal. 5-methylphenazinium methosulfate (PMS) serves as an intermediate electron acceptor to assist the reduction reaction. However, dead microorganism will not generate the succinate dehydrogenase, therefore, the reduction reaction related to MTT and PMS will not occur. Hence, if there is microorganism in the test sample, the microorganism will react with the MTT and PMS in the reacting zone 13 to generate the purple or blue formazan crystal, the users may determine whether the microorganism exists in the test sample based on the blue or purple color change in the reacting zone 13. The transfer rate of the test sample in the microbial detection device 1 may be lowered due to the α-cellulose particle 131 contained in the reacting zone 13. That is, the α-cellulose particle 131 lowers the transfer rate and increases the reaction area, therefore, the reaction signals are enhanced due to the increasing reduction reaction rate with longer reacting time.

Figure 2:
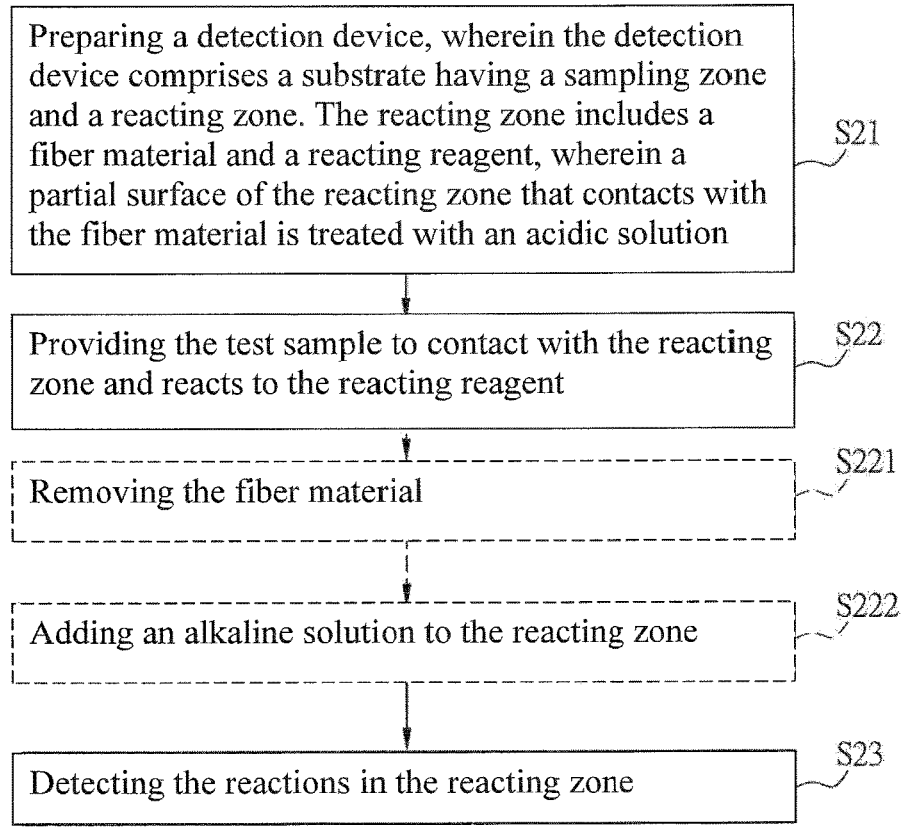
FIG. 2 is another flow chart of the method of manufacturing the microbial detection device of another preferred embodiment of the present invention.
Figure 5:
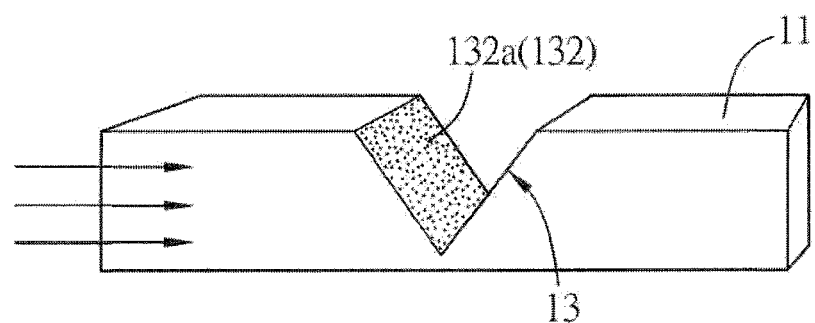
FIG. 5 is the schematic view of the color change in the reacting zone of the microbial detection device shown in FIG. 1B after removing the α-cellulose particles and adding the alkaline solution into the reacting zone.

Please refer to FIG. 2 and FIG. 5, wherein FIG. 5 illustrates the condition of the reacting zone 13 of the microbial detection device 1 after the following steps S221 and S222. Further, in other embodiment, after transferring the test sample from the sampling zone 12 to the reacting zone 13 for reaction (step S22), step S221 and step S222 may further be conducted for observing convenience, wherein step S221: removing the fiber material (α-cellulose particle 131) and step S222: adding an alkaline solution to the reacting zone 13. The alkaline solution may be but not limited to NaOH, KOH, NaHCO$_3$, or Ca(OH)$_2$.

Formazan crystal may deposited at the side surface 132a (a surface 132 of the reacting zone 13 which contacts with the α-cellulose particle) of the V-shaped notch of the reacting zone 13 adjacent to the flowing direction (that is, the longitudinal axis direction shown by the arrow in FIG. 5) because the succinate dehydrogenase carried by the living microorganism will react reductively with PMS and MTT to generate purple or blue formazan crystal. Accordingly, removing the α-cellulose particle 131 is beneficial for the users to better observe the color change on the surface 132a. Also, the alkaline solution may provide the hydroxyl ions to assist the electron transfer, and may further assist the reduction reaction between the reaction reagents adhering to the surface 132a, such as PMS and MTT, and the succinate dehydrogenase carried by the microorganism, so that the reaction signals may be enhanced (enhancing the color of surface 132a).

Figure 6:
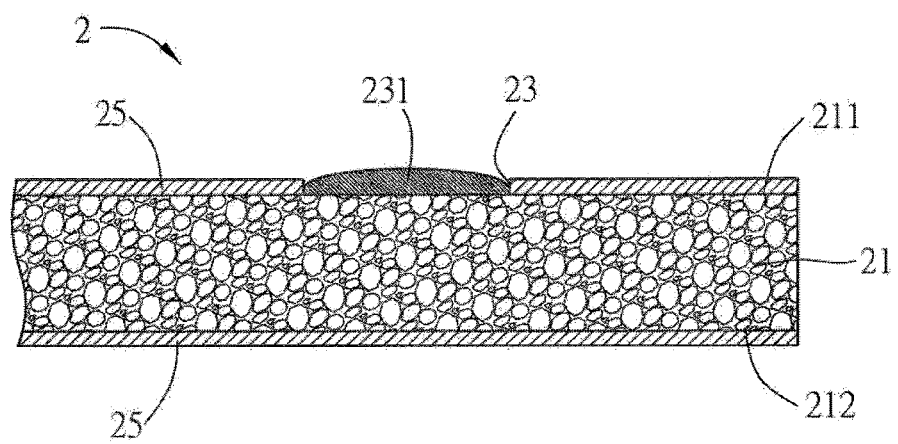
FIG. 6 is the schematic view of another microbial detection device of the present invention.

Please refer to FIG. 6, which illustrate another microbial detection device of the preferred embodiment. As illustrated in the figure, the structure of the present microbial detection device 2 is essentially the same as that of the aforementioned microbial detection device 1, however, additional surface treatment for treating the substrate 21 of the microbial detection device 2 may be performed to improve the stability of the substrate 21, that is, hydrophobic layers 25 are disposed on the upper surface 211 and the lower surface 212 of the substrate 21 of the microbial detection device 2, and the reacting zone 23 is defined by the hydrophobic layer 25. The surface treatment is not limited to hydrophobic treatment, and the hydrophobic reagent comprising but not limited to PDMS (Polydimethylsiloxane) may be coated on at least partial of the upper surface 211 and the lower surface 212 of the substrate 21. The hydrophilic region of the reacting zone 23 may further be narrowed and defined by the aforementioned treatment so that the test sample may be accurately transported to the reacting zone 23 via the other untreated surface of the substrate 21 that retains the hydrophilic property and react with the reaction reagent. Refer to FIG. 6, the surface of the reaction zone 23 that contacts with the α-cellulose particles 231 comprises abundant hydroxyl groups.

The methods of hydrophobic treatment are not limited in the present invention. In practice, the upper surface 211 and/or the lower surface 212 of the microbial detection device 2 may be coated with nail polish or photoresist layer. Specifically, when SU-8 epoxy-based negative photoresist is used as a hydrophobic reagent, the area irradiated by UV light does not be dissolved in the photoresist developer and becomes the hydrophobic layer 25 while the area not irradiated by UV light maintains its hydrophilic property. The similar methods for forming the hydrophobic layer should be known by a skilled person in the art, therefore these methods need not be repeated.

Figure 7A:
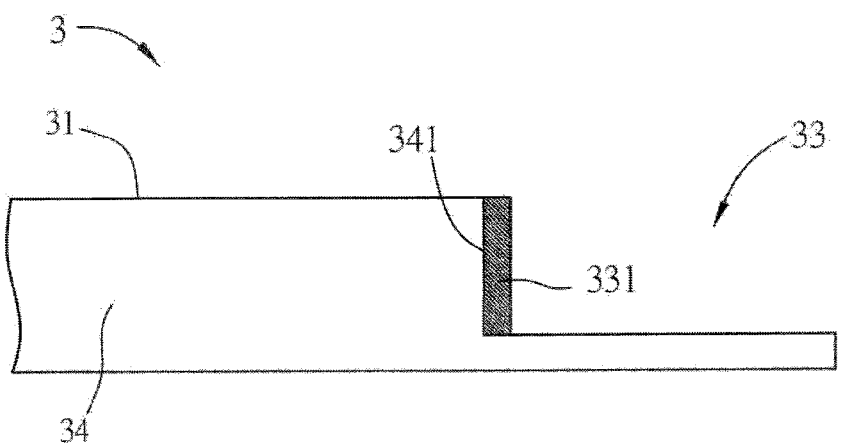
FIG. 7A is the schematic view of another microbial detection device of the present invention.
Figure 7B:
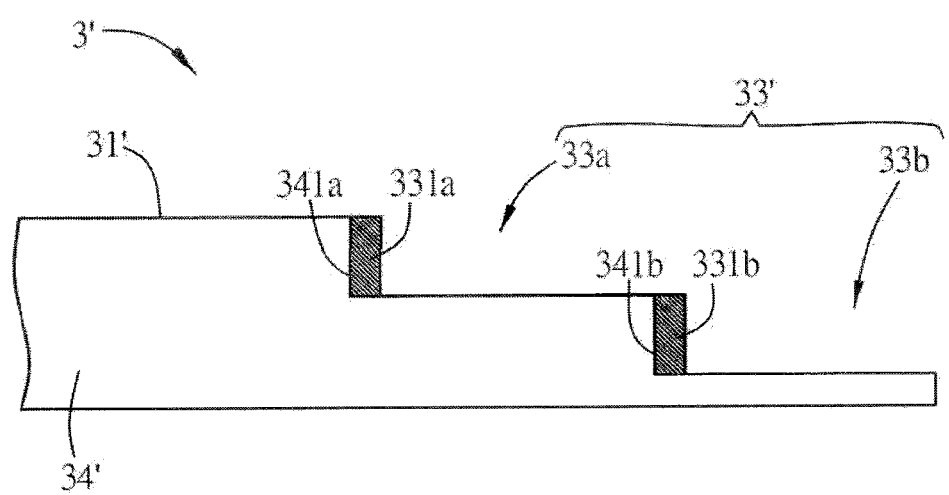
FIG. 7B is the schematic view of another microbial detection device of the present invention.

Please refer to FIGS. 7A and 7B which illustrate another microbial detection device of the preferred embodiment. As illustrated in FIG. 7A, the structure of the present microbial detection device 3 is essentially the same as that of the aforementioned microbial detection device 1, however, the reacting zone 33 of the microbial detection device 3 is a opened notch and is disposed on the sectional surface 341 of the transporting zone 34. That is, the reacting zone 33 is disposed at the terminal of the substrate 31, and the α-cellulose particles 331 are disposed on the sectional surface 341 of the transporting zone 34.

Furthermore, please refer to FIG. 7B, the device is used for detecting different microorganisms in one test sample simultaneously. As illustrated in the figure, the structure of the present microbial detection device 3' is essentially the same as that of the aforementioned microbial detection device 1; however, the reacting zone 33' of the microbial detection device 3' includes two opened notches, which are a first reacting zone 33a and a second reacting zone 33b. The first reacting zone 33a and the second reacting zone 33b are disposed on the sectional surface 341a and 341b of the transporting zone 34'. That is, the reacting zone 33' is disposed at the terminal of the substrate 31', and the α-cellulose particles 331a and 331b are disposed on the sectional surfaces 341a and 341b of the transporting zone 34'. Different types of reaction reagents may be added to the α-cellulose particles 331a and 331b coated on the sectional surfaces 341a and 341b, and the first reacting zone 33a and the second reacting zone 33b to detect different microorganisms in one test sample.

Figure 9A:
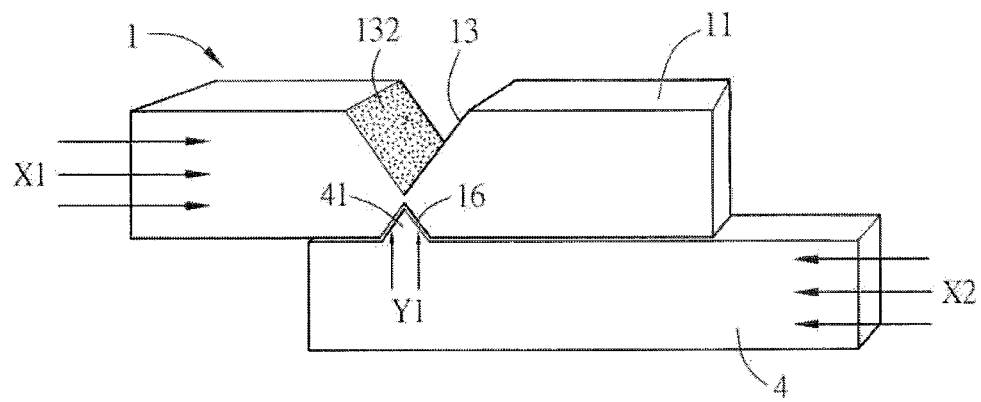
FIG. 9A is the schematic view of another microbial detection device of the present invention.
Figure 9B:
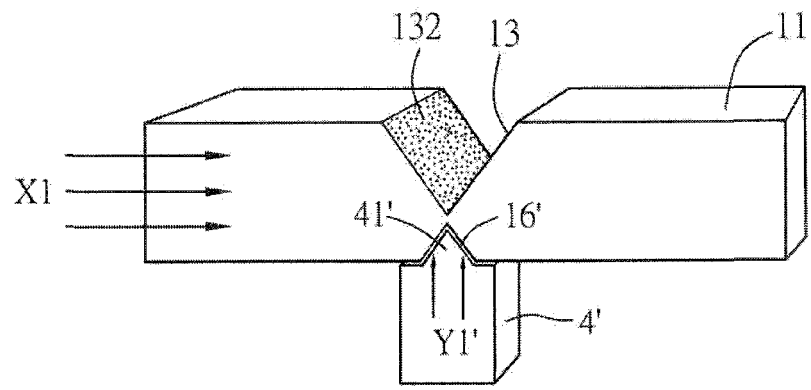
FIG. 9B is the schematic view of another microbial detection device of the present invention.
Figure 9C:
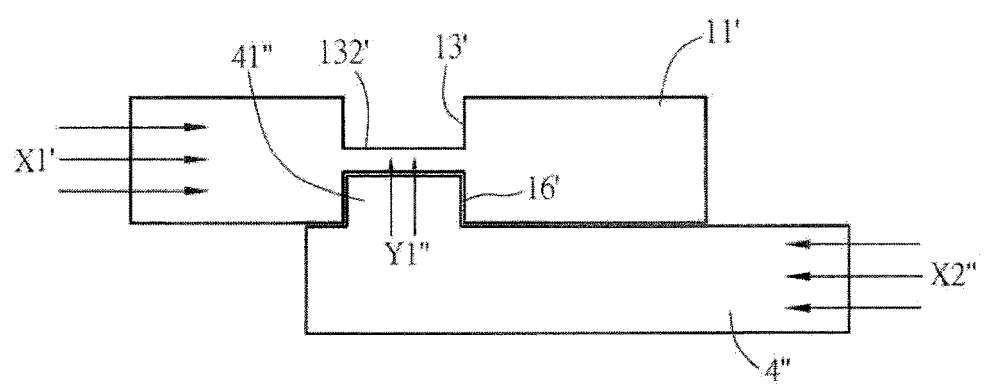
FIG. 9C is the schematic view of another microbial detection device of the present invention.

In addition, please refer to FIG. 9A to FIG. 9C, which illustrate another microbial detection device of the present embodiment. Refer to FIG. 9A, for improving the operational convenience of the step of adding the alkaline solution (step S222), a second substrate 4 is provided in the present example, and a recess portion 16 is disposed under the reacting zone 13 of the substrate 11 of the microbial detection device 1. The second substrate 4 includes a protruded portion 41; the configuration of the protruded portion 41 is preferably corresponding to the recess portion 16 as long as the protruded portion 41 and the recess portion 16 may engage with each other. The alkaline solution may be loaded on the second substrate 4 by soaking or other similar methods. At the meantime, after the substrate 11 engage to the second substrate 4, the alkaline solution will move along the longitudinal direction (that is, the moving direction X2) of the second substrate 4, and move through the recess portion 16 and reach the reacting zone in the transporting direction Y1. The transporting direction Y1 is essentially perpendicular to the moving direction X1 of the test sample when the test sample moves from the sampling zone (not shown in the figure) to the reacting zone 13. Also, the transfer rate of transferring the alkaline solution to the reacting zone 13 through the recess portion 16 will be accelerated if the hydrophilicity of the substrate 11 is higher than that of the second substrate 4. As a result, the color change on the surface 132 will also be accelerated.

Please refer to FIG. 9B, the difference between the second substrate 4' and the aforementioned second substrate 4 is that the second substrate 4' illustrated in FIG. 9B only includes the protruded portion 41' and the main body slightly extending from the protruded portion 41', that is, the second substrate 4' does not include the main body of the second substrate 4 illustrated in FIG. 9A which extends along the longitudinal direction. The other features and the corresponding connecting relation of the second substrate 4' and the substrate 11 are essentially the same as described above and need not be repeated herein. At the meantime, when the substrate 11 engaged to the second substrate 4', the alkaline solution is transported to the reacting zone through the recess portion 16 in the transporting direction Y1'. The transporting direction Y1' is essentially perpendicular to the moving direction X1 of the test sample which moves from the sampling zone (not shown in the figure) to the reacting zone 13. As a result, the color change on the surface 132 will also be enhanced.

Please refer to the second substrate 4" illustrated in FIG. 9C, the difference between the second substrate 4" and the second substrate 4 illustrated in FIG. 9A is that the shape of the protruded portion 41" of the second substrate 4" is a square, and the corresponding recess portion 16' of the substrate 11' is also configured as a square. The features and the corresponding connecting relation of the second substrate 4" and the substrate 11' are the same as described above and need not be repeated herein. Also, at the meantime, after the substrate 11' engages with the second substrate 4", the alkaline solution moves along the longitudinal direction of the second substrate 4' (that is, the moving direction X2") and passes through the recess portion 16' and reach the reacting zone 13' in the transporting direction Y1" via the second substrate 4", wherein the transporting direction Y1" is essentially perpendicular to the moving direction X1' of the test sample which moves from the sampling zone (not shown in figure) to the reacting zone 13'. As a result, the color change on the surface 132' will also be enhanced.

It should be noted that partial surface of the second substrate 4, 4', and 4" illustrated in FIG. 9A to FIG. 9C may be hydrophobic treated. Preferably, the surfaces other than the contact surfaces between the protruded portions 41, 41', 41" of the second substrates 4, 4', 4" and recess portions 16, 16' of the substrates 11, 11' may be hydrophobic treated for further defining and narrowing the areas where the alkaline solution is transported to the substrate 11, 11' from the second substrate 4, 4', 4". As a result, the test sample may be precisely transported to the reacting zone 13, 13' by the areas retaining the hydrophilic property where is not hydrophobic treated, and the color change on the surface 132, 132' will also be enhanced. The embodiments of the hydrophobic reagents are same as that described above, which need not be repeated.

The present invention also provides another preferred embodiment, which is a microbial detection kit, which comprises the microbial detection device and an acidic solution. The microbial detection device comprises a substrate; the substrate includes a sampling zone and a reacting zone, wherein the reacting zone includes α-cellulose particles and a reacting reagent. The acidic solution is utilized for treating the α-cellulose particles and the hydroxyl groups on a surface of the reacting zone which contacts with the α-cellulose particles. The reacting reagent comprises at least two reagents, wherein the first one is selected from the group consisting of 5-methylphenazinium methosulfate and diaphorase; and the second one is selected from the group consisting of 3-(4,5-Dimethylthiazol-2-yl)-2,5-diphenyltetrazolium bromide (MTT), 2-(4-iodophenyl)-3-(4-nitrophenyl)-5-phenyl-2H-tetrazoliumchloride (INT), water-soluble tetrazolium salts (WSTs), and (2,3-bis-(2-methoxy-4-nitro-5-sulfophenyl)-2H-tetrazolium-5-carboxanilide (XTT). In a preferred embodiment, the details of each component, the variation embodiments, and the connecting relations regarding other elements of the microbial detection kit are the same as described in the aforementioned embodiments, which need not be repeated herein.

In addition, the present invention also provides a microbial detection device, which comprises a substrate, wherein the substrate includes a sampling zone and a reacting zone. The reacting zone includes α-cellulose particles and a reacting reagent. The α-cellulose particles and the hydroxyl groups on a surface of the reacting zone which contact with the α-cellulose particles are treated with an acidic solution. The reacting reagent comprises at least two reagents, wherein the first one is selected from the group consisting of 5-methylphenazinium methosulfate and diaphorase; and the second one is selected from the group consisting of 3-(4,5-Dimethylthiazol-2-yl)-2,5-diphenyltetrazolium bromide (MTT), 2-(4-iodophenyl)-3-(4-nitrophenyl)-5-phenyl-2H-tetrazoliumchloride (INT), water-soluble tetrazolium salts (WSTs), and (2,3-bis-(2-methoxy-4-nitro-5-sulfophenyl)-2H-tetrazolium-5-carboxanilide (XTT). In a preferred embodiment, the details of each component, the variation embodiments, and the connecting relations regarding other elements of the microbial detection are the same as described in the aforementioned embodiments, which need not be repeated herein.

The following experimental examples are illustrated for specifically describing the microbial detection device and the operation method and effect of the microbial detection device 1 prepared by the aforementioned embodiment. It should be noted that the following descriptions are exemplified for the present invention to be understood and carried out by a person ordinarily skilled in the art. The microbial detection devices or the microbial detection kit of other embodiments may also be applied for the detection, but are not intended to limit the scope of the present invention.

Experimental Example 1: *E. coli* Detection Operated by the Microbial Detection Device First, 0.023 to 0.026 gram of α-cellulose particles were added to the accommodating space S of the reacting zone 13. 4 μL of HCl (15.63 mM) were then added dropwise to the α-cellulose particles 131 contained in the reacting zone 13 for pre-treatment. Next, the reacting reagent 4 μL which contains 3.26 mM PMS (Sigma-Aldrich, St. Louis, Mo.) and 6.03 mM MTT (Invitrogen Life Sciences, Carlsbad, Calif.) were added to the α-cellulose particles 131 contained in the reacting zone 13. The microbial detection device 1 was air-dried at 25° C. for 2 minutes after completing the aforementioned additions.

Next, after the aforementioned processing steps, one terminal of the sampling zone 12 of the microbial detection device 1 was immersed in *E. coli* solutions with sequentially diluted concentrations (0, $4\times10^3$, $4\times10^4$, $4\times10^5$, $4\times10^6$, $4\times10^7$, and $4\times10^8$ colony forming unit, cfu/mL, N=9) for 8 minutes and forcing the *E. coli* solution to move to the reacting zone 13.

Afterward, the α-cellulose particles 131' were removed from the reacting zone 13, and the microbial detection device 1 was air-dried at 25° C. for 45 minutes. Then, 4 µL of NaOH (31.25 mM) was added dropwise into the reacting zone 13 for enhancing the color change in reacting zone 13. Finally, the image of the color change in the reacting zone 13 was captured by digital camera (EOS 5D Mark III, Canon, Japan) and analyzed by the image analysis software (ImageJ Software, NIH, USA) to evaluate the intensity of the color change in the reacting zone 13, and the intensity of the color change was analyzed by linear regression analysis.

Figure 8:
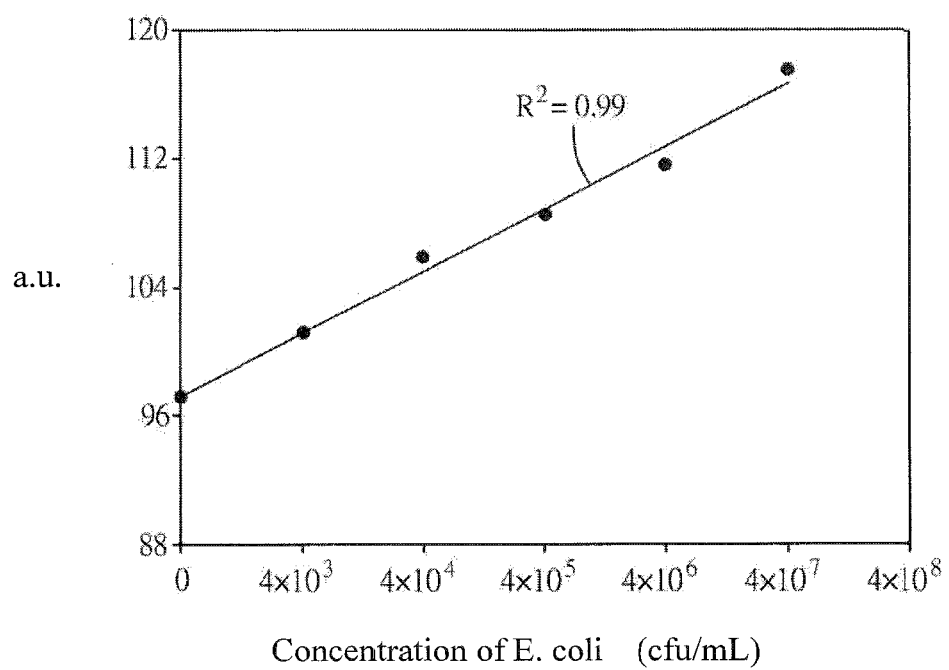
FIG. 8 is the relative intensity of *E. coli* detection using the microbial detection device shown in FIG. 1B.

Please refer to FIG. 8, which illustrates the relative intensity (a.u.) of the *E. coli* detection result using the microbial detection device and following the detection process as describe above. FIG. 8 shows the positive linear correlation ($R^2$=0.99) between the intensity (a.u.) of the color change in the microbial detection device 1 and the concentration of *E. coli* within the concentration ranging from 0 to $10^7$ cfu/mL.

Experimental Example 2: Comparison of the Effects of the Reagents Comprising PMS and MTT w/wo Adding HCl First, 0.023 and 0.026 gram of α-cellulose particles were added to the accommodating space S of the reacting zone 13. 4 µL of HCl (15.63 mM) were then added dropwise to the α-cellulose particles 131 contained in the reacting zone 13 for pre-treatment. Also, another microbial detection device was simultaneously prepared but without adding HCl into the reacting zone 13. Similarly, the reaction reagent comprising 3.26 mM PMS (Sigma-Aldrich, St. Louis, Mo.) and 6.03 mM MTT (Invitrogen Life Sciences, Carlsbad, Calif.) was added dropwise into the α-cellulose particles 131 contained in the reacting zone 13. The microbial detection device 1 was air-dried at 25° C. for 2 minutes after completing the aforementioned additions.

Figure 10:
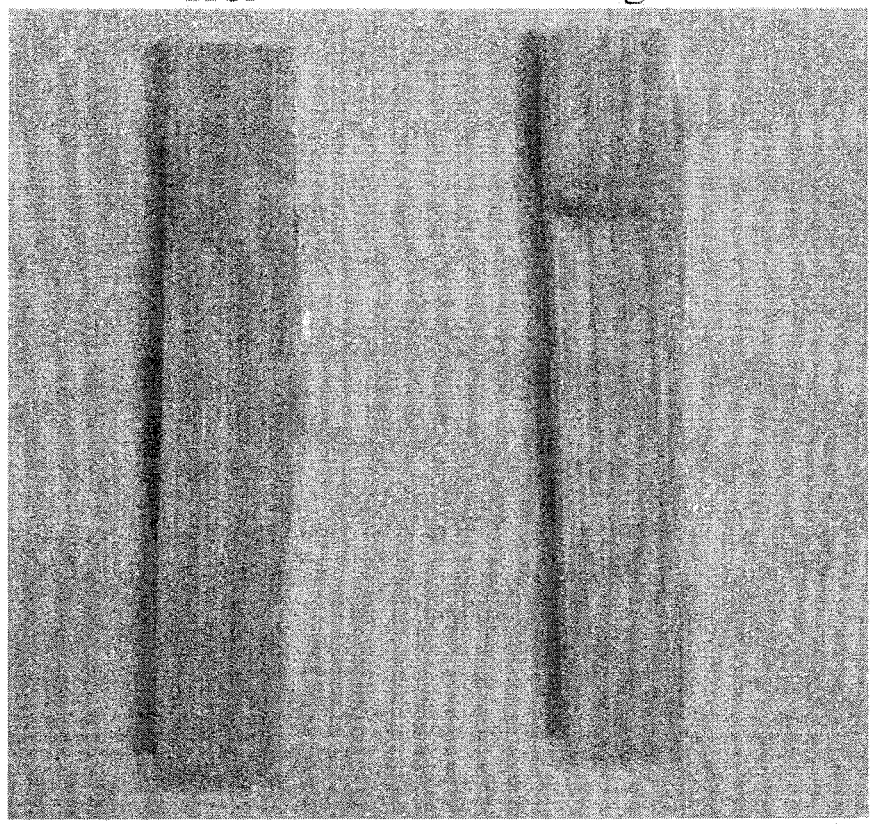
FIG. 10 is the results of the experimental example 2.

As shown in FIG. 10, no reaction took place (no color change) at the reacting zone added with HCl may explain that HCl effectively inhibited the reaction between the reaction reagent (PMS, MTT) and the α-cellulose particles 131. Meanwhile, the color changed at the reacting zone without adding the HCl. The result suggested that adding acidic solution into the α-cellulose particles 131 of the reacting zone 13 may inhibit the effect caused by the hydroxyl groups of the α-cellulose particles 131, and reduce the reactions before reacting with the microorganisms. As a result, the reaction signal may become more apparent.

In summary, in the microbial detection device and method for manufacturing the microbial detection device of the present invention, the reacting zone comprising the chemical reaction reagent is applied to effectively detect a specific detection target, for example, the nitrate or nitrite detection in food safety. Owning to the elements formed of the lignocellulosic substrate in the present invention, the better absorbability to water may enhance the capillarity of the liquid sample in the detection device and increase the detection rate. Also, the conventional test strips need to be processed, and reaction reagents banned for food industry or harmful to human body may be used in the processing steps.

Accordingly, foods to be tested will be inedible if directly contact with those harmful reaction reagents. In contrary, the natural lignocellulosic substrates used in the present invention may directly contact with or even insert into the test sample for the detection, and the test sample remains edible after the detection. Further, the present invention is advantageous of cheaper price, or easy processing. More preferably, the lignocellulosic substrate has better structural strength comparing to that of the conventional test strips due to its robust mechanical structure and acid and alkali resistance.

The aforementioned embodiments or examples are only exemplary, and the present invention is not limited thereto. It is to be understood that many other possible modifications and variations can be made without departing from the spirit and scope of the invention as hereinafter claimed.

What is claimed is:

1. A microbial detection method, comprising steps of:
providing a detection device, wherein the detection device comprises a first substrate, wherein the first substrate comprises a sampling zone and a reacting zone, wherein the reacting zone includes a fiber material and a reacting reagent, wherein the fiber material comprises hydroxyl groups on its surface, and wherein the reacting zone is treated with an acidic solution;
providing a test sample to contact with the reacting zone and react with the reacting reagent, wherein the test sample contacts with the sampling zone, and the test sample is moved from the sampling zone toward the reacting zone to react with the reacting reagent;
removing the fiber material; and
adding an alkaline solution to the reacting zone, wherein the fiber material consists of α-cellulose particles.

2. The microbial detection method as claimed in claim 1, wherein the alkaline solution is transported to the reacting zone in a transporting direction by a second substrate, and the transporting direction is perpendicular to a moving direction of which the test sample moves from the sampling zone to the reacting zone.

3. The microbial detection method as claimed in claim 2, wherein the hydrophilicity of the first substrate is higher than that of the second substrate.

4. The microbial detection method as claimed in claim 1, wherein the first substrate further includes a transporting zone, wherein the transporting zone connects with the sampling zone and the reacting zone, and the reacting zone is disposed on a section of the transporting zone.

5. The microbial detection method as claimed in claim 4, wherein the reacting zone further comprises a first reacting zone and a second reacting zone, which are disposed on different sections of the transporting zone.

6. The microbial detection method as claimed in claim 1, wherein the reacting reagent comprises at least one selected from a group consisting of 5-methylphenazinium methosulfate and diaphorase; and at least one selected from a group consisting of 3-(4,5-Dimethylthiazol-2-yl)-2,5-diphenyltetrazolium bromide (MTT), (2-(4-iodophenyl)-3-(4-nitrophenyl)-5-phenyl-2H-tetrazoliumchloride (INT), water-soluble tetrazolium salts (WSTs), and (2,3-bis-(2-methoxy-4-nitro-5-sulfophenyl)-2H-tetrazolium-5-carboxanilide (XTT).

\* \* \* \* \*